United States Patent
Hallahan et al.

(10) Patent No.: US 7,828,765 B2
(45) Date of Patent: Nov. 9, 2010

(54) METHOD AND DEVICE FOR ADMINISTERING TWO COMPONENTS INTO THE TEAT CANAL OF A NON-HUMAN ANIMAL

(75) Inventors: Stephen Hallahan, Dublin (IE); Nicholas McHardy, County Wicklow (IE); Brendan Smith, Dublin (IE); Louis Van Vessem, Hellevoetsluis (NL)

(73) Assignee: Bimeda Research & Development Ltd, Tallaght Dublin (IE)

( * ) Notice: Subject to any disclaimer, the term of this patent is extended or adjusted under 35 U.S.C. 154(b) by 1579 days.

(21) Appl. No.: 11/047,758

(22) Filed: Feb. 2, 2005

(65) Prior Publication Data

US 2005/0171506 A1     Aug. 4, 2005

Related U.S. Application Data

(60) Provisional application No. 60/540,336, filed on Feb. 2, 2004.

(30) Foreign Application Priority Data

May 24, 2004    (IE) .................................. 2004/0364

(51) Int. Cl.
*A61M 37/00*    (2006.01)
(52) U.S. Cl. .............................. 604/91; 604/89; 604/82
(58) Field of Classification Search ............. 604/82–92, 604/416
See application file for complete search history.

(56) References Cited

U.S. PATENT DOCUMENTS

| | | | |
|---|---|---|---|
| 3,911,916 A | 10/1975 | Stevens | 128/218 |
| 3,912,806 A | 10/1975 | Dowrick et al. | 424/16 |
| 3,923,058 A | 12/1975 | Weingarten | 128/218 |
| 4,049,830 A | 9/1977 | Pugliese | 424/343 |
| 4,172,138 A | 10/1979 | Rhodes | 424/271 |
| 4,313,440 A | 2/1982 | Ashley | 128/218 |
| 4,344,967 A | 8/1982 | Easton et al. | 424/359 |
| 4,439,184 A | 3/1984 | Wheeler | 604/90 |

(Continued)

FOREIGN PATENT DOCUMENTS

EP          0076068          4/1983

(Continued)

OTHER PUBLICATIONS

Twomey et al, J Dairy SCI 83, 2000, pp. 1981-1988, Protection Against Staphylococcus aureus Mastitis in Dairy Cows Using . . . .

(Continued)

*Primary Examiner*—Kevin C Sirmons
*Assistant Examiner*—Catherine N Witczak
(74) *Attorney, Agent, or Firm*—Finnegan, Henderson, Farabow, Garrett & Dunner LLP

(57) ABSTRACT

The invention relates to a method and device for treating or preventing or suppressing a disease or condition in a non-human animal. The method comprises the steps of providing a single delivery device containing two components for sequential delivery from the delivery device. A first component is delivered from the single delivery device into a teat canal of a non-human animal and subsequently the second component is delivered from the single delivery device into the teat canal. The components are delivered without substantial mixing of the components.

31 Claims, 13 Drawing Sheets

U.S. PATENT DOCUMENTS

| | | | | |
|---|---|---|---|---|
| 4,702,737 | A * | 10/1987 | Pizzino | 604/191 |
| 5,102,388 | A | 4/1992 | Richmond | 604/88 |
| 5,195,966 | A | 3/1993 | Corby | 604/75 |
| 5,415,648 | A | 5/1995 | Malay et al. | 604/181 |
| 5,476,449 | A | 12/1995 | Richmond | 604/87 |
| 5,593,384 | A | 1/1997 | Halem | 604/54 |
| 6,077,252 | A | 6/2000 | Siegel | 604/214 |
| 6,107,344 | A | 8/2000 | Loosemore | 514/635 |
| 6,270,482 | B1 | 8/2001 | Rosoff et al. | 604/200 |
| 6,558,358 | B2 | 5/2003 | Rosoff et al. | 604/200 |
| 6,723,074 | B1 | 4/2004 | Halseth | 604/201 |
| 2003/0167041 | A1 * | 9/2003 | Rosoff et al. | 604/232 |
| 2003/0236503 | A1 | 12/2003 | Koenig et al. | 604/201 |
| 2004/0004316 | A1 | 1/2004 | Robertson | 267/64 |

FOREIGN PATENT DOCUMENTS

| | | |
|---|---|---|
| EP | 0081896 | 6/1983 |
| EP | 0271306 | 6/1988 |
| EP | 0540493 | 5/1993 |
| EP | 0755663 | 1/1997 |
| EP | 0971690 | 9/2002 |
| FR | 2076853 | 10/1971 |
| FR | 2251339 | 6/1975 |
| GB | 1441747 | 7/1976 |
| GB | 1456349 | 11/1976 |
| GB | 2273441 | 6/1994 |
| GB | 2273443 | 6/1994 |
| GB | 2273655 | 6/1994 |
| JP | 2003-299734 | 10/2003 |
| RU | 2028798 | 2/1995 |
| WO | WO94/13261 | 6/1994 |
| WO | WO95/31180 | 11/1995 |
| WO | WO96/32482 | 10/1996 |
| WO | WO98/26759 | 6/1998 |
| WO | WO02/11793 | 2/2002 |
| WO | WO02/076534 | 10/2002 |
| WO | WO03/022245 | 3/2003 |
| WO | WO2004/039434 | 5/2004 |

OTHER PUBLICATIONS

Meaney, VET REC, 1976, 1 pg., Dry Period teat seal.
Meaney, IR J Agric Res 16, 1977, pp. 293-299, Effect of a Dry Period Teat Seal on Bovine Udder Infection.
Farnsworth et al, Jayma vol. 177, No. 5, 1980, pp. 441-444, Use of a Teat Sealer for Prevention of Intramammary Infections in . . . .
Robert, Dictionnaires Le Robert, 1993, pp. 347-397.
Leon-Barua et al, Rev Of Infectious Diseases 12:1, Jan.-Feb. 1990, pp. S24-S29, In Vitro and In Vivo Effects of Three Bismuth . . . .
Vogt et al, ZBL Bakt 271, 1989, pp. 304-310, The Minimum Inhibitory Concentrations of Various Bismuth Salts against . . . .
Kirk et al, Encyclopedia of Chemical Technology vol. 2, 1948, pp. 77-84 and 538-540.
Kollidon, BASF, May 1996, pp. 18-21, Polyvinylpyrrolidone for the pharmaceutical industry.
Osmonds Teat Seal, 4 pgs.
http://www.proagri.co.za/uitgawe_07/7-05_Cloxamast-eh.htm, 9 pgs., Sep. 1996.
Berry et al, J Dairy SCI, vol. 85, 2002, pp. 2512-2520, The effect of an intramammary test seal on new intramammary . . . .

* cited by examiner

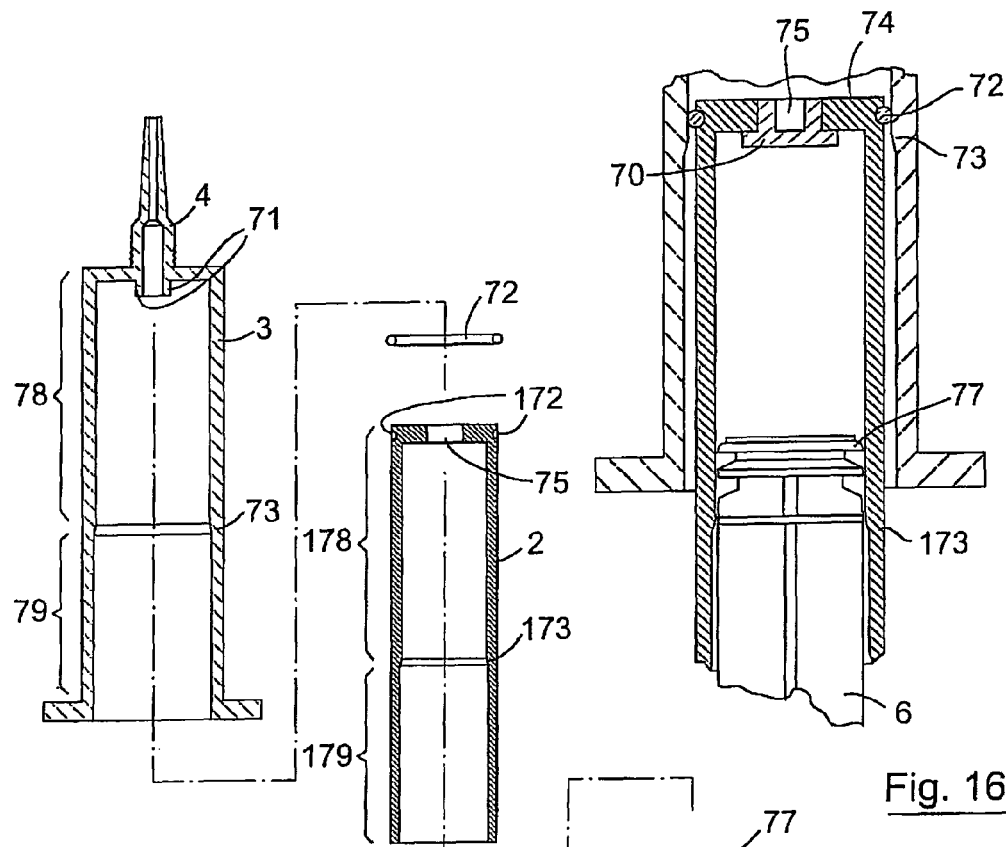
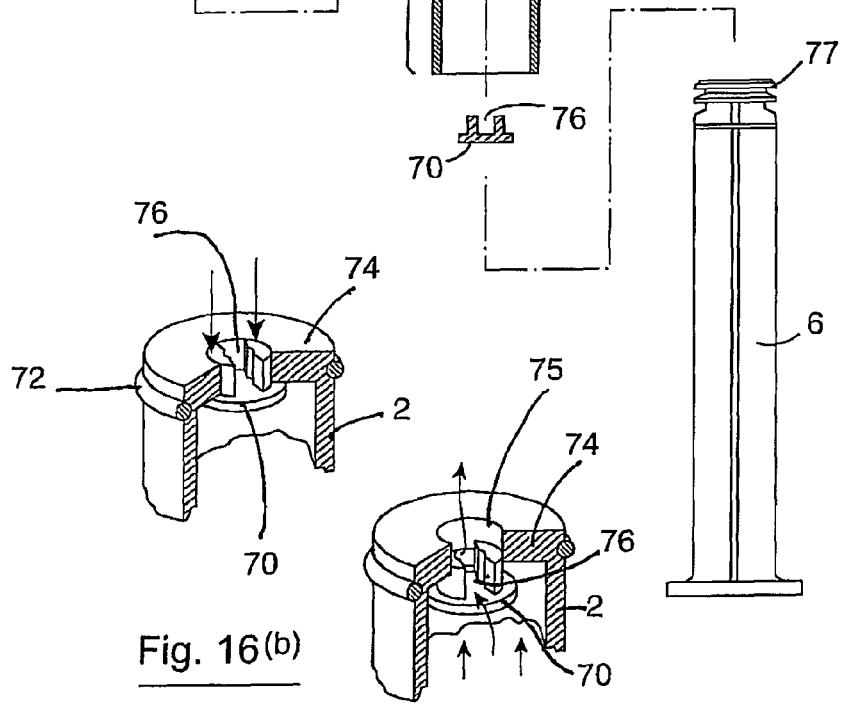
Fig. 16(a)
Fig. 15
Fig. 16(b)
Fig. 16 (c)

METHOD AND DEVICE FOR ADMINISTERING TWO COMPONENTS INTO THE TEAT CANAL OF A NON-HUMAN ANIMAL

This is a complete application claiming benefit of provisional 60/540,336 filed Feb. 2, 2004.

INTRODUCTION

The invention relates to a method and device for administering two components into the teat canal of a non-human animal.

Bovine mastitis is a severe, potentially fatal, inflammatory disease of the udder, caused by a broad range of infectious organisms, but most notably by various Gram positive bacteria of the genera Staphylococcus and Streptococcus and the Gram negative species, Escherichia coli. The infection usually enters the udder via the teat or streak canal. Mastitis is treated by a variety of antibiotic cerates, infused into the udder via the teat or streak canal. In severe cases, high doses of antibiotic are also given by injection. A high proportion of mastitic infections are contracted during the "dry" period, which precedes calving. The infection may later become clinically significant either during the dry period, or after calving when lactation has resumed.

It is known to treat mastitis using a twin injector pack, one injector containing an anti-bacterial formulation and a second injector containing a seal or barrier formulation. The anti-bacterial formulation is delivered first to the teat canal followed by delivery of the seal formulation forming a physical barrier in the teat canal against the entry of bacteria into the udder. These twin injector packs are sold under the name Teat Seal™. WO94/13261 and WO95/31180 describe the twin injectors in detail and are hereby incorporated by reference.

While the twin injector system provides an effective method to reduce the incidence of clinical mastitis administration of the injectors can be time consuming, doubles the risk of introducing extraneous environmental bacteria and doubles the risk of causing damage to the epithelium of the streak canal. The use of two injectors also increases the cost of treatment and creates additional non-degradable waste.

There is a need for an improved method and device for preventing intrammary disorders which will overcome at least some of these problems.

STATEMENTS OF THE INVENTION

According to the invention there is provided a method for treating or preventing or suppressing a disease or condition in a non-human animal comprising the steps of:—
  providing a single delivery device containing two components for sequential delivery from the delivery device;
  delivering a first component from the single delivery device into a teat canal of a non-human animal; and
  subsequently delivering the second component from the single delivery device into the teat canal without substantial mixing of the components.

In one embodiment the delivery device comprises an injector device containing the two components, the components being separated by a barrier and the method comprises the steps of:—
  delivering the first component from the injector device;
  at least partially releasing the barrier; and
  subsequently delivering the second component from the injector device.

In another embodiment the disease or condition is mastitis and the method of the invention is for treating or preventing a mastitis-causing micro-organism.

In a further embodiment the second component comprises a seal.

According to a further aspect the invention provides a method for treating, preventing or suppressing mastitis or a mastitis causing micro-organism comprising the steps of sequentially delivering from a single delivery device an antimicrobial formulation and a seal formulation into the teat canal of a non-human animal wherein the antimicrobial formulation and the seal formulation are delivered into the teat canal without substantial mixing of the formulations prior to delivery into the teat canal.

In one embodiment the seal formulation comprises a non-toxic heavy metal salt.

In another embodiment the seal formulation comprises greater than 40% by weight of the heavy metal salt.

In a further embodiment the seal formulation comprises between 50% and 75% by weight of the heavy metal salt.

In one embodiment the seal formulation comprises approximately 65% by weight of the heavy metal salt.

In another embodiment the heavy metal is bismuth.

In a further embodiment the salt is a sub-nitrate salt.

In one embodiment the seal formulation comprises a gel base.

In another embodiment the gel base is a gel based on aluminium stearate.

In a further embodiment the gel base includes liquid paraffin as a vehicle.

In one embodiment the first component comprises an antimicrobial.

In another embodiment the antimicrobial is selected from any one or more of betalactam antibiotics, polymyxins, glycopeptides, aminoglycosides, lincosamides, macrolides, pleuromutilins, "fenicols" such as chloramphenicol and florfenicol, tetracyclines, sulphonamides and potentiated sulphonamides such as mixtures of trimethoprim and one or more sulphonamide, quinolones and fluoroquinolones, ionophores, courmarins such as novobiocin, natural or synthetic peptides, aminoglycosides, antimicrobial peptides or antimicrobials, lantibiotics, or other products of bacteria and other micro-organisms.

In a further embodiment the betalactam is selected from any one or more of penicillin, modified penicillin such as cloxacillin, amoxycillin, ampicillin, cephalosporins or beta lactam antibiotics potentiated by beta lactamase inhibitors such as clavulanic acid.

In one embodiment the aminoglycoside is selected from any one or more of streptomycin, dihydrostreptomycin, neomycin, gentamycin, framycetin, aparamycin or kanamycin.

In another embodiment the antimicrobial is selected from any one or more of macrolide, lincosamide or pleuromutilin, erythromycin, spiramycin, tylosin, spiramycin, tilmicosin, lincomycin, spectinomysin, pirlimycin or tiamulin.

In a further embodiment the antimicrobial is selected from any one or more of potentiated sulphonamide mixtures, trimethoprim plus sulphadiazine, sulphadimidine, sulphadoxine, sulphadimethoxine or other sulphonamide, oxytetracycline, minocycline or doxycycline, fluoroquinolones, enrofloxacin, ciprofloxacin, norfloxacin, danofloxacin, difloxacin or marbofloxacin.

In one embodiment the first component comprises an anti-inflammatory.

In another embodiment the anti-inflammatory is selected from any one or more of steroids such as prednisolone, betamethazone, dexamethazone, phenylbutazone, or non-steroids such as flunixin, ketoprofen, carprofen, vedaprofen, meloxicam, tepoxalin, eltenac, nimesulide or tolfenamic acid.

According to further aspect of the invention there is provided an injector device for delivery of components into the teat canal of a non-human animal comprising:
- a barrel for containing a first component,
- an outlet nozzle at one end of the barrel,
- an internal receptacle for containing a second component,
- a barrier for separating a first component and a second component, and
- a delivery means for delivery of a first component from the barrel and sequential delivery of a second component from the internal receptacle through the outlet nozzle.

In one embodiment the barrier is normally closed.

In another embodiment the barrier is releasable for delivery of the second component.

In a further embodiment the barrier is defined by at least a portion of the internal receptacle.

In one embodiment the barrier comprises one or more passageways.

In another embodiment the one or more passageways are opened when the barrier is released for delivery of the second component through said one or more passageways.

In a further embodiment the device comprises an activator for releasing the barrier.

In one embodiment the activator comprises a mechanical activator means.

In another embodiment the activator comprises at least one projecting member.

In a further embodiment the activator is located in the barrel.

In one embodiment the activator is located adjacent to the outlet nozzle.

In another embodiment the activator comprises one or more passageways.

In a further embodiment the activator is configured for engagement with the internal receptacle to provide a direct passageway for delivery of the second component from the internal receptacle into the outlet nozzle.

In one embodiment the delivery means comprises a plunger for the barrel.

In another embodiment the barrier is released by the delivery means.

In a further embodiment the internal receptacle comprises an inner barrel located within an outer barrel defined by the barrel of the injector.

In one embodiment the inner barrel is a close fit within the outer barrel.

In another embodiment the delivery means comprises the inner barrel.

In a further embodiment the inner barrel defines a plunger for the outer barrel.

In one embodiment the delivery means comprises a plunger for the inner barrel.

In another embodiment the inner barrel comprises engagement means for engagement with the outer barrel on assembly.

In a further embodiment the engagement means comprises an external seal.

In one embodiment the outer barrel comprises engagement means for engagement with the inner barrel.

In another embodiment the outer barrel comprises a locking ring for engagement with the inner barrel.

In a further embodiment the inner barrel comprises engagement means for engagement with the plunger.

In one embodiment the inner barrel comprises a locking ring for engagement with the plunger.

In another embodiment the receptacle comprises a bag.

In a further embodiment the receptacle comprises a capsule.

In one embodiment the receptacle is attached to or forms an integral part of the delivery means.

In another embodiment the activator comprises a rupturing means for at least partially releasing the barrier.

In a further embodiment the rupturing means comprises a mechanical rupture member.

In one embodiment the rupture member comprises at least one blade.

In another embodiment the rupture member comprises at least one tooth.

In a further embodiment the rupture member is located in the barrel.

In one embodiment the rupture member is located adjacent to the outlet nozzle.

In another embodiment the barrel contains a first component.

In a further embodiment the first component comprises an antimicrobial formulation.

In one embodiment the internal receptacle contains a second component.

In another embodiment the second component comprises a seal formulation.

In a further embodiment a first component is delivered from the barrel and a second component is subsequently delivered from the internal receptacle without substantial mixing of the components.

In one embodiment the seal formulation may comprise the seal formulation as described above.

In another embodiment the antimicrobial formulation may comprise the antimicrobial formulation as described above.

BRIEF DESCRIPTION OF THE DRAWINGS

The invention will be more clearly understood from the following description thereof given by way of example only with reference to the accompanying drawings, in which:—

FIG. 15 is an exploded broken out view of components of the injector of FIG. 14;

FIG. 16(*a*) is a detailed cross sectional view of a portion of the injector of FIG. 14, and FIGS. 16(*b*) and 16(*c*) are detailed perspective views of a portion of the device in the configurations of FIGS. 14(*b*) and (*c*) respectively;

DETAILED DESCRIPTION

Figure 1:
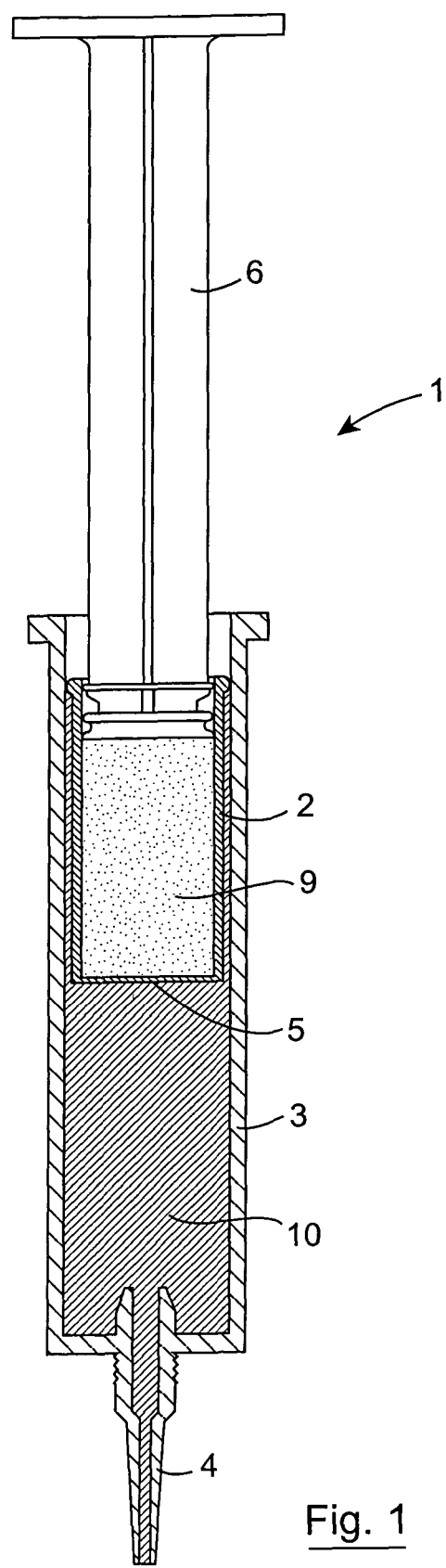
FIG. 1 is a schematic cross sectional view of an injector device according to the invention.
Figure 2:
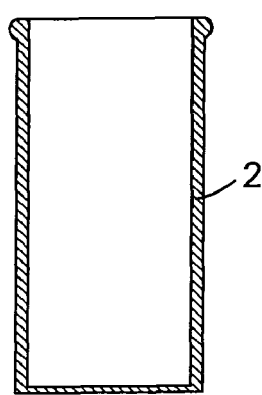
FIG. 2 is a cross sectional view of an internal barrel of the device.
Figure 3:
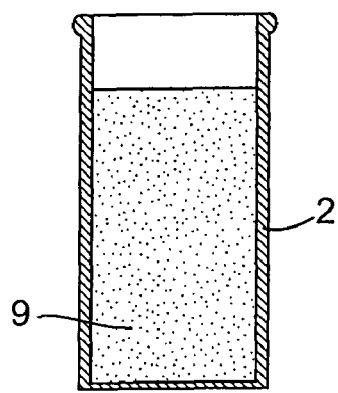
FIG. 3 is a cross sectional view of the internal barrel of FIG. 2 with a seal component in place.
Figure 4:
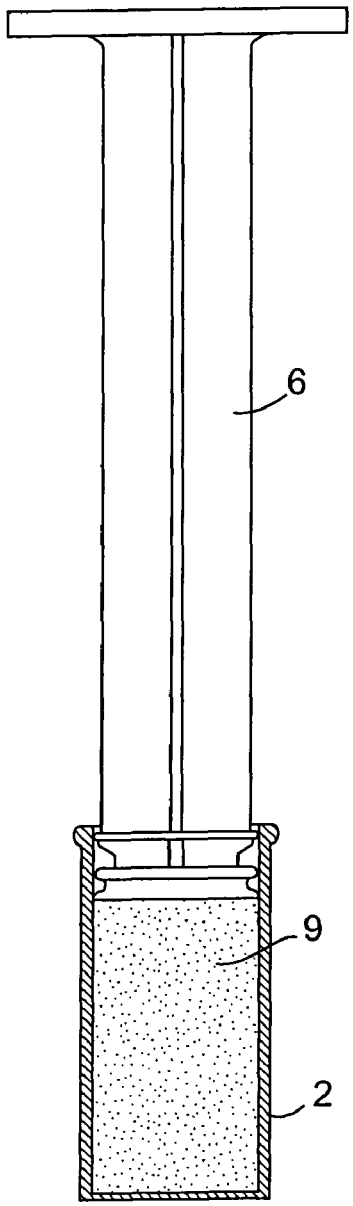
FIG. 4 is a cross sectional view of the internal barrel of FIG. 3 with a plunger inserted.
Figure 5:
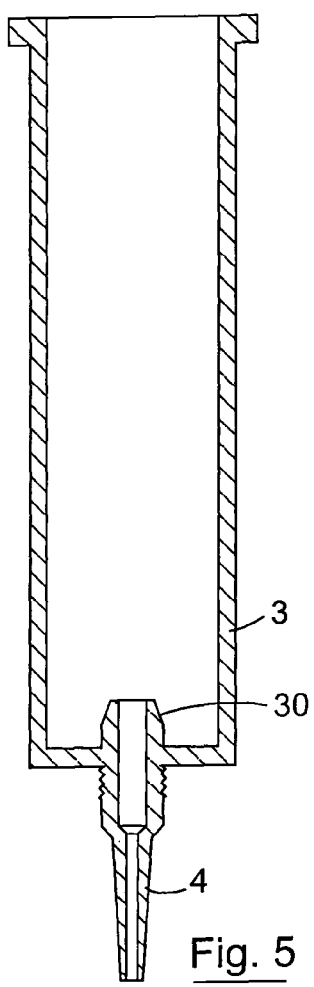
FIG. 5 is a cross sectional view of an external barrel of the device.
Figure 6:
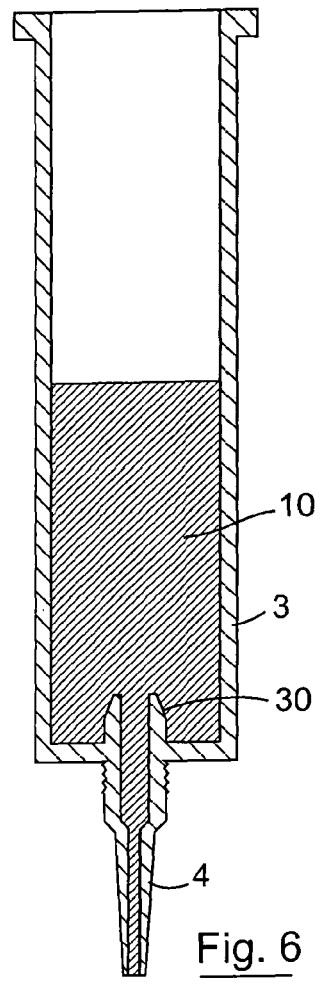
FIG. 6 is a cross sectional view of the external barrel of FIG. 5 with an antimicrobial component in place.
Figure 7:
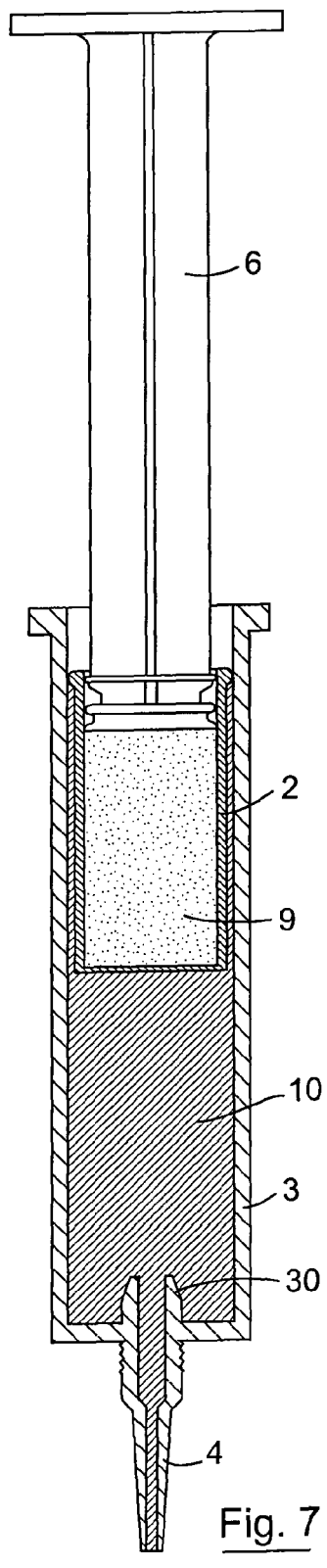
FIG. 7 is a cross sectional view of the assembled injector device.
Figures 8A, 8B, 8C:
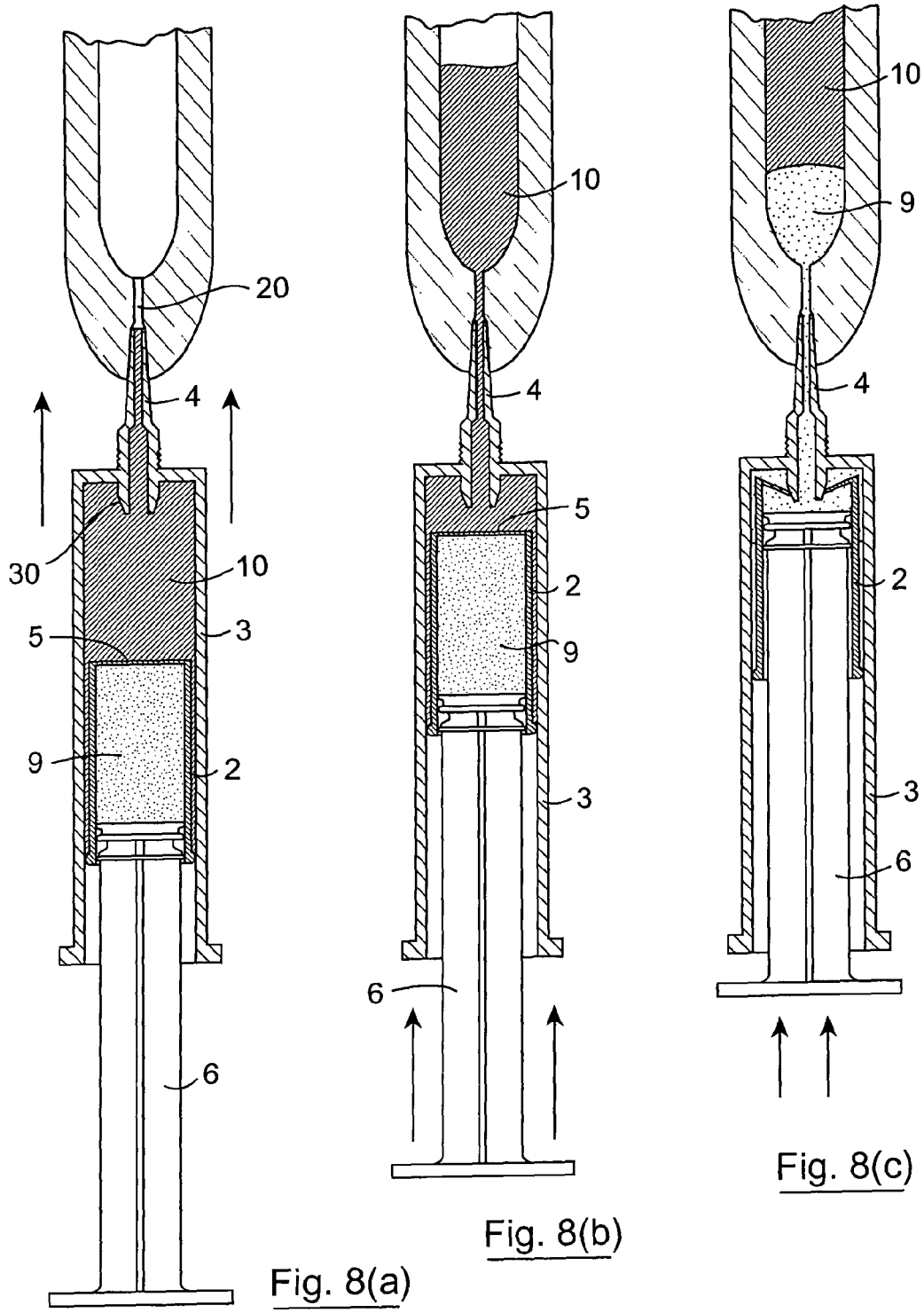
FIGS. 8(a) to 8(c) are cross sectional views of the injector device, in use.

The invention provides an injector device that allows for the sequential delivery of two incompatible components such as an antimicrobial formulation and a seal formulation into the teat canal of a non-human animal. The seal formulation and antimicrobial formulation are contained separately within a single injector device. This enables the product to be stored without affecting the stability of either component. The device also provides for the delivery of the antimicrobial formulation ahead of the seal formulation which effectively forms a physical barrier in the teat canal preventing any further entry into the teat canal. The seal formulation also prevents the possibility of the antimicrobial phase leaking or being expressed from the teat by gravitational or hydrostatic forces.

The seal formulation may comprise a viscous oil-based cerate containing a high proportion of a heavy metal salt, bismuth subnitrate. The product Teat Seal (trade mark of Cross Vetpharm Group) is described in detail in WO98/26759 and comprises a non-toxic heavy metal salt in a gel base. The base is a gel based on aluminium stearate. The gel preferably includes a vehicle such as liquid paraffin. The gel may also comprise a polyethylene gel. The gel may be based on low density polyethylene or on high density polyethylene. Preferably, the heavy metal salt is present in an amount of greater than 40%, preferably between 50% and 75% by weight, most preferably approximately 65% by weight.

The seal formulation prevents infection entering the udder via the teat or streak canal through a combination of its viscosity, density and adhesiveness.

The antimicrobial or anti-inflammatory formulation may be selected from any one or more of a wide variety of compounds that are known to be effective for the treatment, prevention and elimination of mastitis and mastitis-causing organisms, including inter alia gram positive and gram negative bacteria, yeasts, fungi and rickettsias. The antimicrobial or anti-inflammatory materials may include inter alia beta lactam antibiotics such as penicillins and cephalosporins, beta lactam antibiotics potentiated by beta lactamase inhibitors such as clavulanic acid, polymyxins, glycopeptides, aminoglycosides, lincosamides, macrolides, pleuromutilins, "fenicols" such as chloramphenicol and florfenicol, tetracyclines, sulphonamides and potentiated sulphonamides such as mixtures of trimethoprim and one or more sulphonamide, quinolones and fluoroquinolones, ionophores, coumarins such as novobiocin, natural or synthetic peptides, lantibiotics, and other antimicrobial products of bacteria and other microorganisms.

Other antimicrobials may be selected from any one or more of macrolide, lincosamide or pleuromutilin, erythromycin, spiramycin, tylosin, spiramycin, tilmicosin, lincomycin, spectinomysin, pirlimycin, tiamulin, potentiated sulphonamide mixtures, trimethoprim plus sulphadiazine, sulphadimidine, sulphadoxine, sulphadimethoxine or other sulphonamide, oxytetracycline, minocycline or doxycycline, fluoroquinolones, enrofloxacin, ciprofloxacin, norfloxacin, danofloxacin, difloxacin or marbofloxacin.

The second component may be selected from any one or more of anti-inflammatory compounds, steroids such as prednisolone, betamethazone, dexamethasone, phenylbutazone, or non-steroids such as flunixin, ketoprofen, carprofen, vedaprofen, meloxicam, tepoxalin, eltenac, nimesulide or tolfenamic acid.

Other antimicrobial or anti-inflammatory compounds used in the treatment of intramammary infections in non-human animals may also be used.

These antimicrobial or anti-inflammatory materials may be formulated either singly or in combinations of two or more compounds as liquids, cerates, solutions, suspensions emulsions or flowable powders in water, oil (of animal, vegetable, mineral or other origin) or other organic vehicles. Other excipients such as solubilising, suspending or emulsifying agents, viscosity modifiers, surfactants, encapsulating agents and other means to adjust the rate at which the compound(s) is released from the formulation, buffers and such agents to maintain the pH of the formulation, anti-inflammatory agents such as various steroidal and non-steroidal compounds commonly used for this purpose, and various preservative agents commonly used in pharmaceutical preparations.

Referring to the drawings an initially to FIGS. 1 to 8 there is illustrated an injector device 1 according to the invention. The injector device 1 in this case comprises an inner barrel 2 and an outer barrel 3. The outer barrel 3 has a nozzle 4. The inner barrel 2 contains a first component comprising a seal 9. The barrel 2 has a barrier or membrane 5 at its distal end. A plunger 6 is inserted into proximal end of the inner barrel 2 above the seal component 9. An antimicrobial or anti-inflammatory component 10 is contained within the outer barrel 3 below the inner barrel 2. In use, the nozzle 4 is inserted into a teat canal 20 of a non-human animal such as a cow. The inner barrel 2 is pushed through the outer barrel 3 by the plunger 6 to expel the antimicrobial or anti-inflammatory component 10 (FIG. 8(*a*)). When the antimicrobial or anti-inflammatory component 10 has been expelled (FIG. 8(*b*)) the plunger 6 on the inner barrel 2 is further depressed to expel the seal 9 from the inner barrel 2. The pressure of the plunger 6 may be sufficient to release or rupture the barrier/membrane 5 on the inner barrel 2 allowing the seal 9 to be expelled from the injector device through the nozzle 4 and into the teat canal (FIG. 8(*c*)). Rupturing means such as teeth 30 situated within the outer barrel 3 adjacent to the outlet nozzle 4, may be used to release or rupture or open the barrier/membrane 5.

Figure 9:
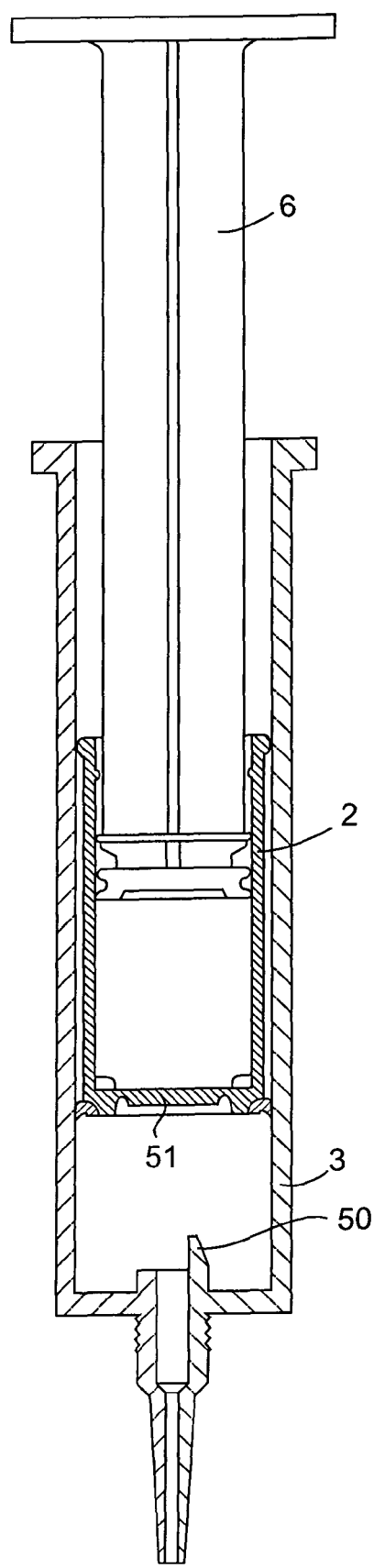
FIG. 9 is a cross sectional view of another injector of the invention.
Figure 9A:
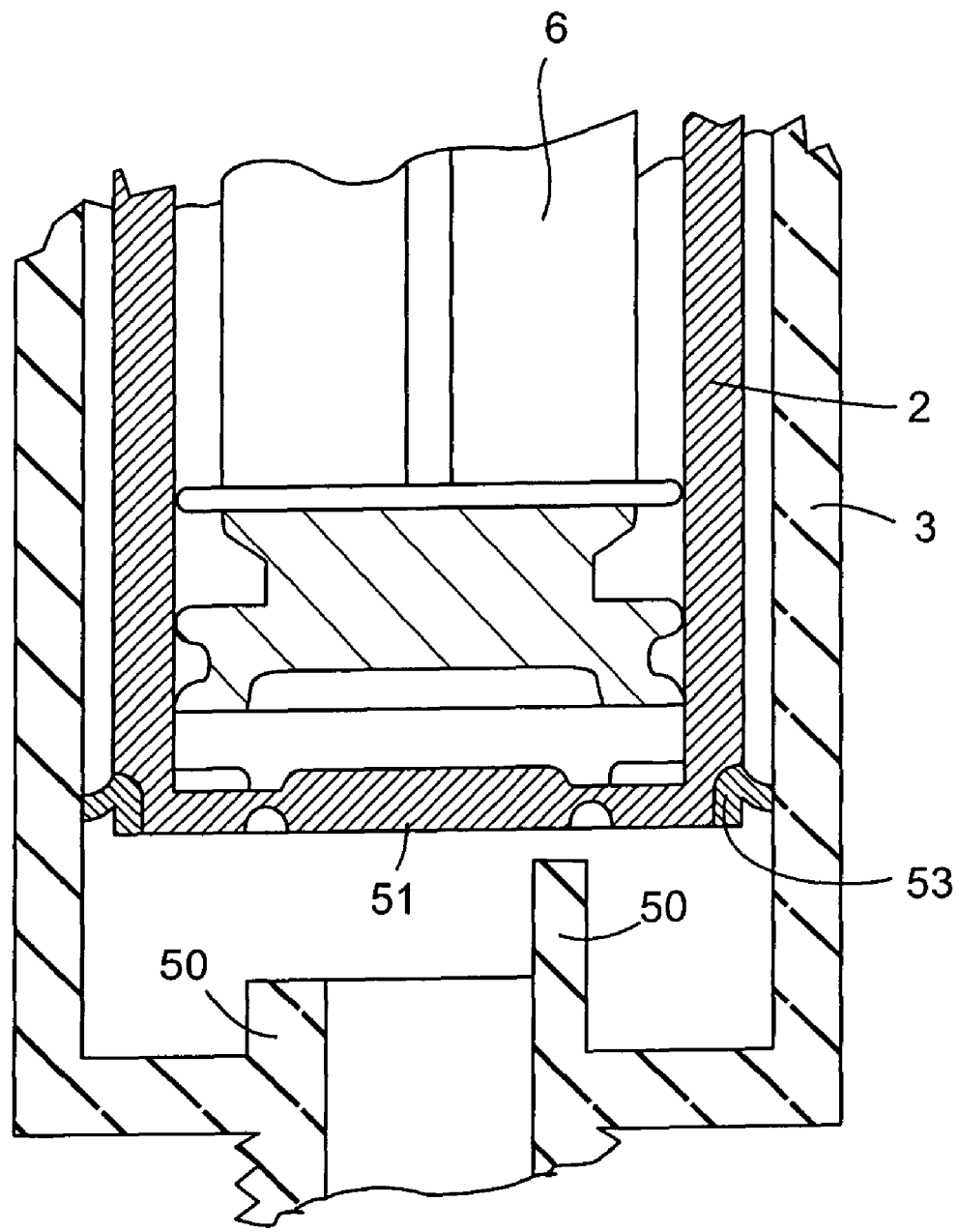
FIG. 9(a) is an enlarged view of portion of the injector in FIG. 9.
Figure 13:
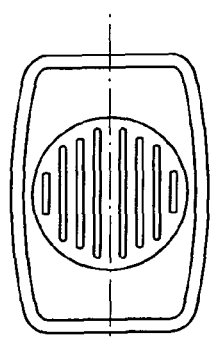
FIG. 13 is a top plan view of the device of FIG. 9.
Figure 10:
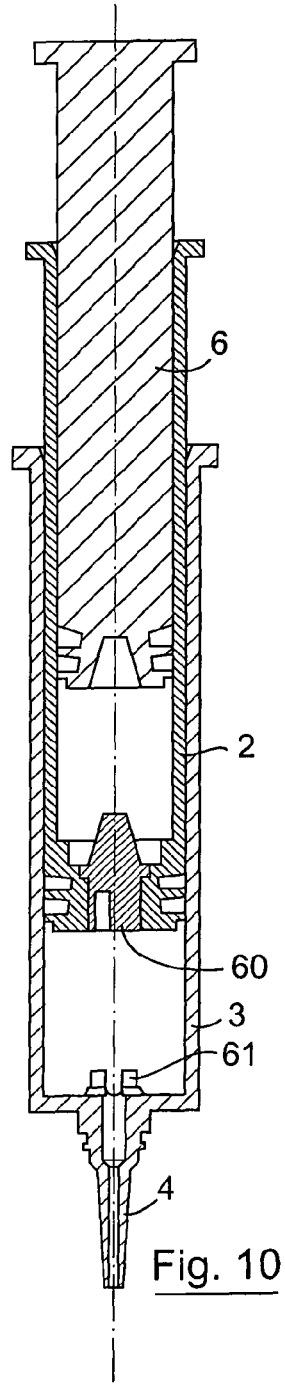
FIGS. 10 to 12 are cross sectional views of a further injector device according to the invention in different configurations of use.
Figure 11:
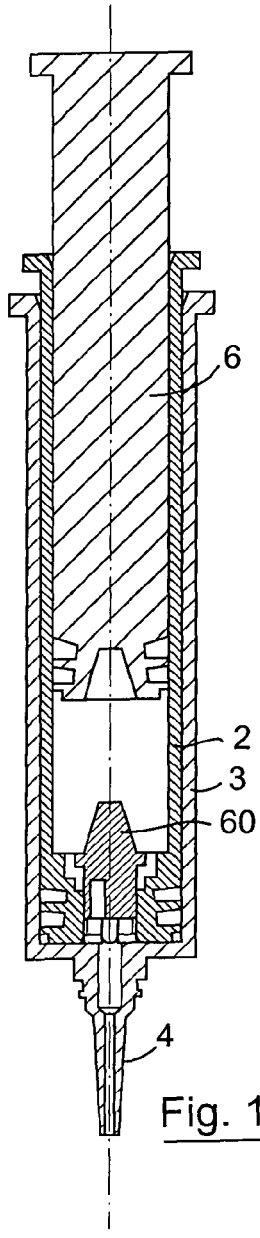
Figure 12:
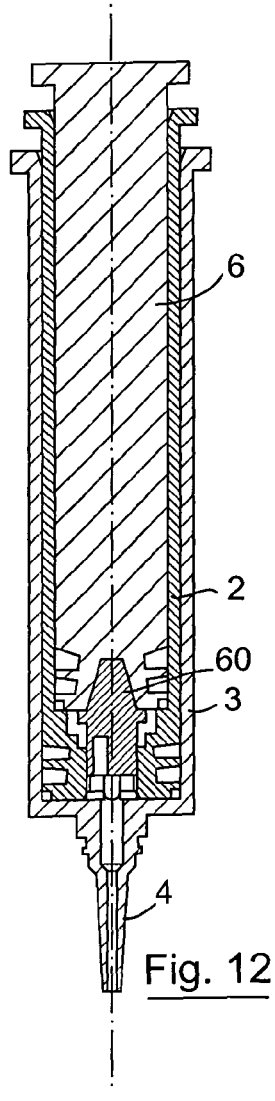

Referring to FIGS. 9 and 9(*a*) there is illustrated another injector which is similar to the injector of FIGS. 1 to 8 and like parts are assigned the same reference numerals. The injector device 1 comprises an inner barrel 2 and an outer barrel 3. The outer barrel 3 has a nozzle 4. In this case the barrier is released by an activator defined by a number of spikes 50 projecting upwardly to different lengths. The membrane/barrier has a portion 51 which is knocked-out by the spikes 50 to allow ejection of the seal component. The distal end of the inner barrel 2 has a seal or frill 53 which seals with the inner wall of the outer barrel 3.

Referring to FIGS. 10 to 13 there is illustrated a further injector which is again similar to that of FIGS. 1 to 8 and like parts are assigned the same reference numerals. The injector device 1 comprises an inner barrel 2 and an outer barrel 3. The outer barrel 3 has a nozzle 4. In this case the barrier comprises a valve 60 at the distal end of the inner barrel 2. An activator 61 projects upwardly from the lower wall of the outer barrel. In use, when the inner barrel 2 is in the configuration of FIG. 11 the valve 60 is lifted by engagement with the activator 61 and allows the seal component 9 in the inner barrel 2 to pass through the injector nozzle 4.

When the plunger 6 is pushed down, the inner barrel 2 also travels down through the outer barrel 3. The outside of the inner barrel 2 is a close fit in the outer barrel 3 so that the inner barrel 2 itself acts as a delivery device or plunger for delivery of the first component from the outer barrel 3 through the nozzle 4.

Figures 14A, 14B, 14C:
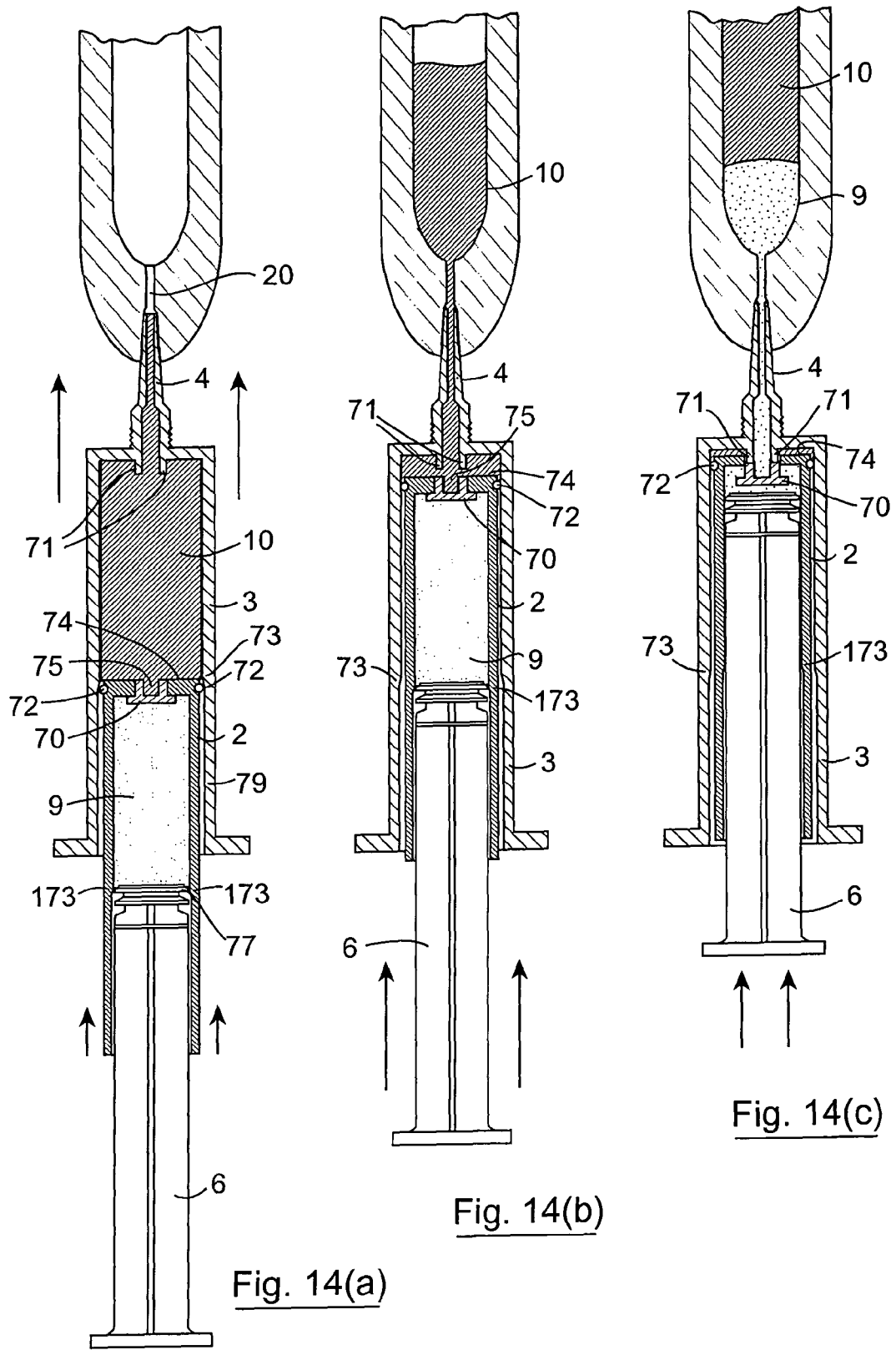
FIGS. 14(*a*) to 14(*c*) are cross sectional views of a further injector device according to the invention in different configurations of use.

Referring to FIGS. 14 to 16 there is illustrated another injector which is again similar to the injector of FIGS. 1 to 13 and like parts are assigned the same reference numerals. The injector device comprises an inner barrel 2 and an outer barrel 3. The outer barrel 3 has a nozzle 4. The inner barrel 2 contains a seal component 9. A plunger 6 is inserted into proximal end of the inner barrel 2 above the seal component 9. Antimicrobial 10 is contained within the outer barrel 3. In use, the nozzle 4 is inserted into a teat canal 20. The inner barrel 2 comprises a distal end 74 having an outlet 75 and the barrier comprises a valve 70 which is received in the outlet 75. The valve 70 is normally closed (FIGS. 14(*a*), (*b*)) during delivery of the first component from the outer barrel 3. An activator 71 projects upwardly from the lower wall of the outer barrel 3. In use, when all of the first component has been delivered and the inner barrel 2 is in the configuration of FIG. 14(*c*) the valve 70 is released by engagement with the activator 71 and the seal component 9 in the inner barrel 2 is allowed to pass through side passageways 76 in valve through the outlet 75 and into the injector nozzle 4.

The inner wall of the inner barrel 2 is formed for engagement with the plunger 6 and comprises a locking ring 173 between the proximal and distal ends thereof. The inner barrel 2 comprises a distal portion 178 and a proximal portion 179, the distal portion 178 having an internal diameter less than the internal diameter of the proximal portion 179. The plunger 6 comprises a seal 77 which passes over the locking ring 173 of the inner barrel on assembly and the plunger 6 is thus sealingly engaged with the inner barrel 2.

The inner barrel 2 further comprises an external seal 72 for engagement with the internal wall of outer barrel 3. The external seal 72 may for example comprise an integrally formed seal or an o-ring housed in a recess 172 in the external side wall of the inner barrel 2. The external seal 72 is located near the distal end 74 of the inner barrel.

The internal wall of the outer barrel 3 is formed for engagement with the inner barrel 2 and comprises a locking ring 73 between the proximal and distal ends thereof for engagement with the external seal 72 of the inner barrel 2. The outer barrel 3 comprises a distal portion 78 and a proximal portion 79. The distal portion 78 having an internal diameter less than the internal diameter of the proximal portion 79. The external seal 72 passes over locking ring 73 of the outer barrel 3 on assembly and sealingly engages the outer barrel. The antimicrobial or anti-inflammatory formulation 10 is thus prevented from passing between the barrels as the plunger 6 is depressed.

The valve 70 comprises a plurality of channels 76 which are exposed when the valve 70 is released to allow the seal component to pass out through the valve. Thus upon releasing of the valve the channels 76 which define a passageway for the seal component are opened.

The activator 71 defines a substantially cylindrical form defining a passageway and corresponds in form to the outlet 75 enabling it to be received in a portion of the outlet. The activator 71 is a close fit with the outlet 75.

In use the inner barrel 2 is pushed through the outer barrel 3 by the plunger 6 to expel the antimicrobial 10 (FIG. 14(*a*)). The outside of the inner barrel 2 has the geometry of the plunger 6 so that the inner barrel 2 itself acts as a plunger. When the antimicrobial 10 has been expelled (FIG. 14(*b*)) the plunger 6 on the inner barrel 2 is further depressed to expel the seal 9 from the inner barrel 2. The valve 70 is released by engagement of the inner barrel with the activator 71 and the seal component 9 in the inner barrel 2 is allowed to pass through the valve passageways into the injector nozzle 4 and is expelled into the teat canal (FIG. 14(*c*)).

Referring to FIGS. 14 to 16, and in particular FIGS. 16(*b*) and (*c*) the operation of the valve is described in more details.

When closed the valve 70 which is a close fit with the outlet 75 rests in the outlet and prevents any mixing of the components in the outer and inner barrels (FIGS. 14(*b*) and 16(*b*)).

When the activator 71 is received in the outlet 75 (FIGS. 14(*c*) and 16(*c*)) the valve is released and the passageways 76 in the valve are opened to enable the seal component to pass into the valve passageways 76 through the passageway defined by the activator 71 and into the injector nozzle 4.

The engagement of the activator 71 with the outlet of the inner barrel 2 provides for alignment of the respective passageways 76 of the valve and the activator before the valve is released and the seal component is allowed to pass from the inner barrel. The respective passageways 76 of the valve and activator provide a closed and isolated pathway for the seal component to pass from the inner barrel 2 directly into the injector nozzle 4.

One advantage of a valve type barrier of this embodiment is that there is not risk of any part of the barrier becoming mobile. The barrier is retained with the injector.

Figure 17:
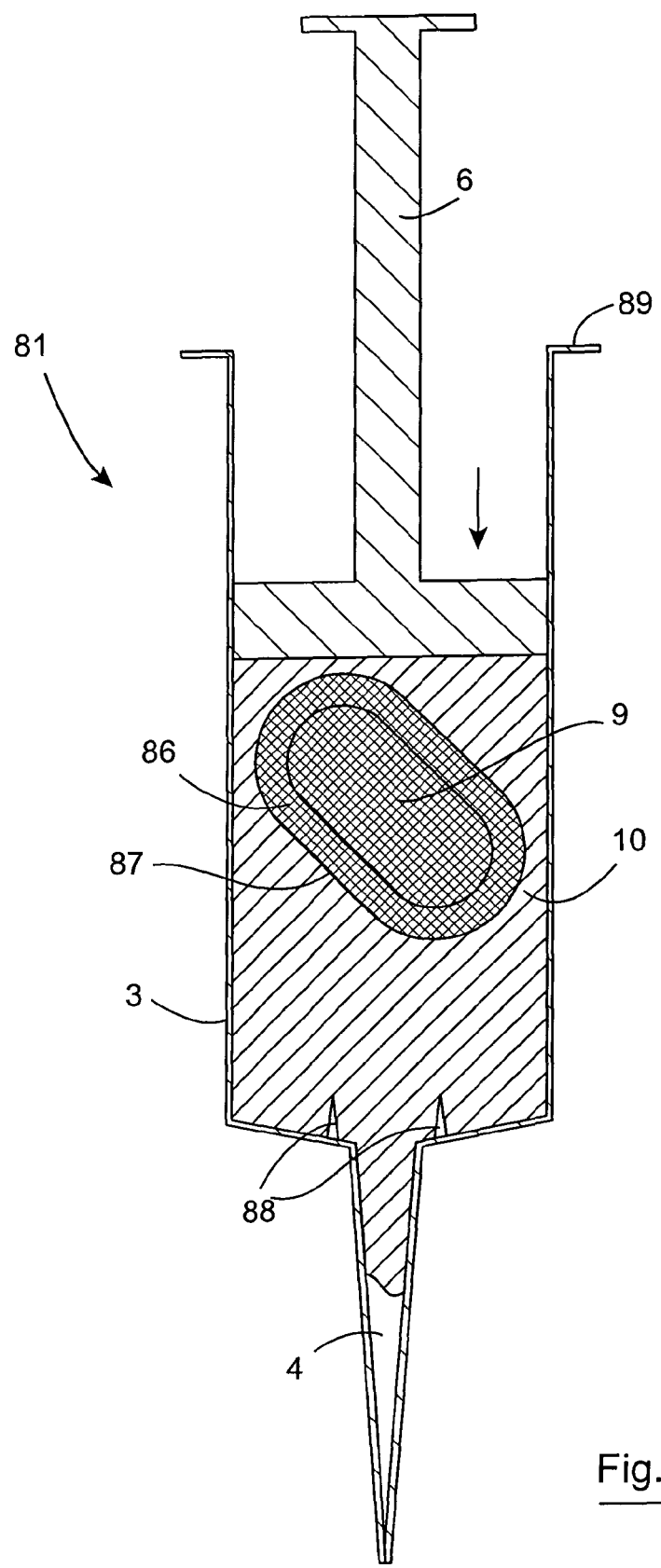
FIG. 17 is a schematic cross sectional view of an injector device according to a further embodiment of the invention.
Figure 18:
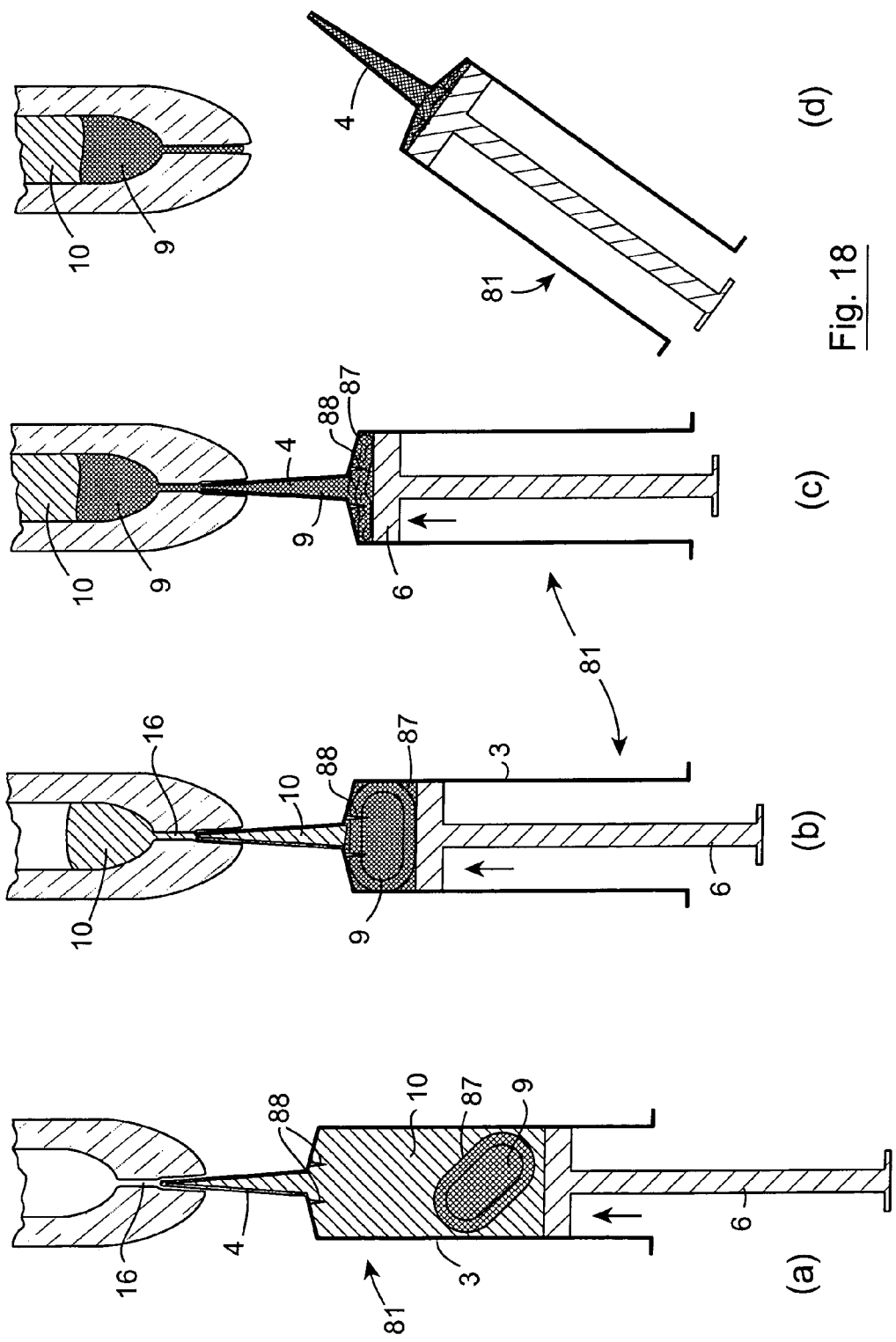
FIGS. 18(*a*) to 18(*d*) are cross sectional views of the device of FIG. 17, in use.

Referring to FIGS. 17 to 18 there is illustrated an injector device 81 of an alternative embodiment of the invention (which is similar to the injector of FIGS. 1 to 16 and like parts are assigned the same reference numerals). The injector device 81 comprises a barrel 3, an outlet nozzle 4 and a plunger 6. Two incompatible components 9 and 10 are placed within the barrel 3 of the injector device 81. The two components such as an antimicrobial 10 and a seal 9 are separated from one another by a barrier/membrane. The antimicrobial 10 is placed in the barrel 3 and a seal 9 is placed in a receptacle 86 such as a bag which is defined by an outer membrane 87 which provides the barrier.

The receptacle 86 may comprise a capsule into which the seal is filled on manufacture. The capsule may then be readily dropped into the barrel 3 of the injector before a plunger 6 is inserted.

When the nozzle 4 of the device 81 is inserted into a teat canal 16 a user depresses the plunger 6 to effect delivery of the antimicrobial 10 from the injector device into the teat canal (FIG. 17(*a*)). After the antimicrobial 10 is expelled from the injector device further pressure applied to the plunger results in puncturing or bursting of the receptacle 86 allowing egress of the seal 9 which is delivered into the teat canal (FIG. 17(*b*)). FIG. 17(*d*) shows the position of a seal formulation 9 and antimicrobial formulation 8 on delivery into the teat of a non-human animal.

The injector device may comprise rupturing means such as sharp teeth 88 at the distal end of the barrel 3 to assist in puncturing or bursting the receptacle 86.

It will be appreciated that for ease of manufacture and use, the receptacle 86 may be attached to the plunger 6. In this case the receptacle is unable to come into contact with the rupturing device until substantially all of the first component has been expelled from the device.

When delivering a seal 9 and antimicrobial or anti-inflammatory formulation 10 into the teat canal of a non-human animal the injector device is typically positioned vertically below the teat with the delivery nozzle uppermost. The seal formulation 9 has a much higher specific gravity than the antimicrobial or anti-inflammatory formulation 10 and therefore the receptacle containing the seal formulation remains at the lower end of the barrel 3 containing the antimicrobial or anti-inflammatory formulation during the delivery of the anti-microbial or anti-inflammatory formulation into the teat. In this case the receptacle comes into contact with the rupturing device only when substantially all of the antimicrobial or anti-inflammatory formulation has been delivered into the teat.

Figure 19:
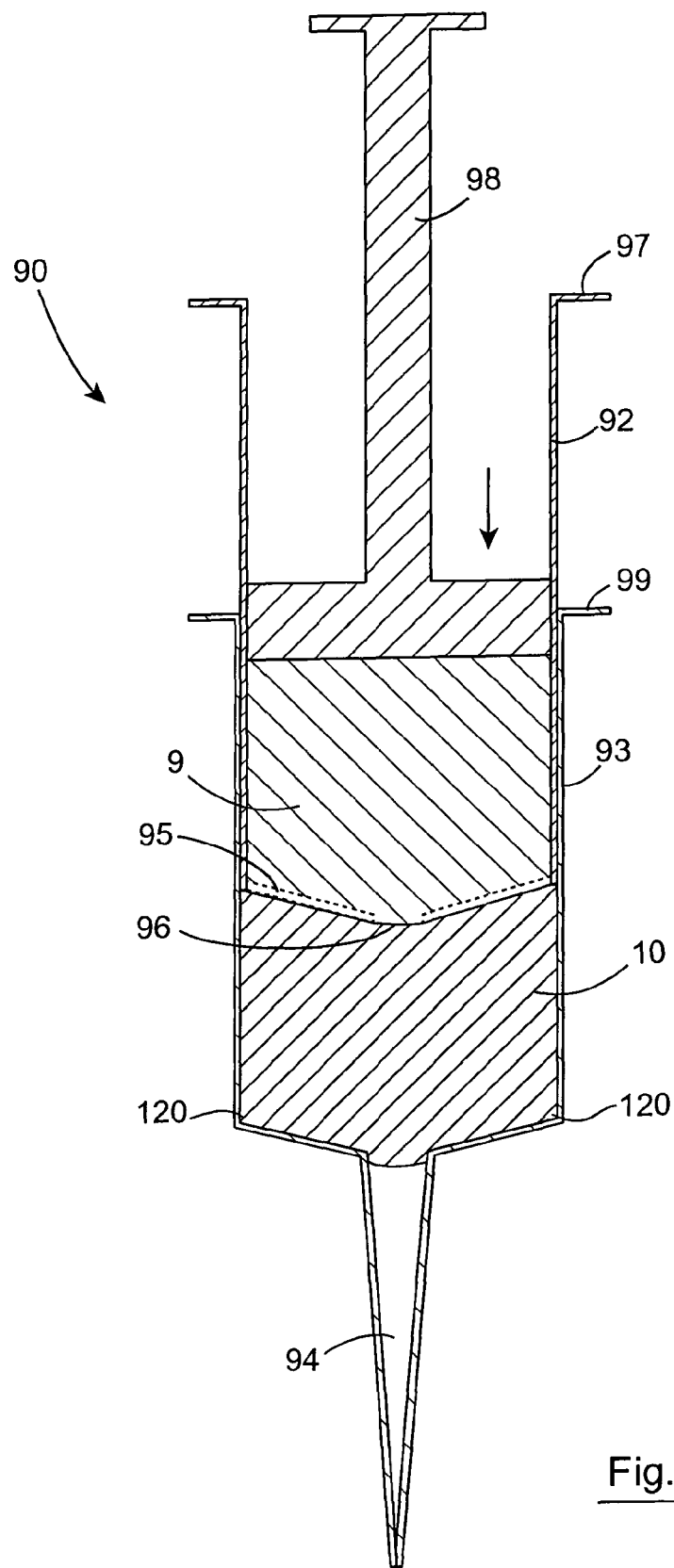
FIG. 19 is a schematic cross sectional view of another injector device according to the invention.
Figure 20:
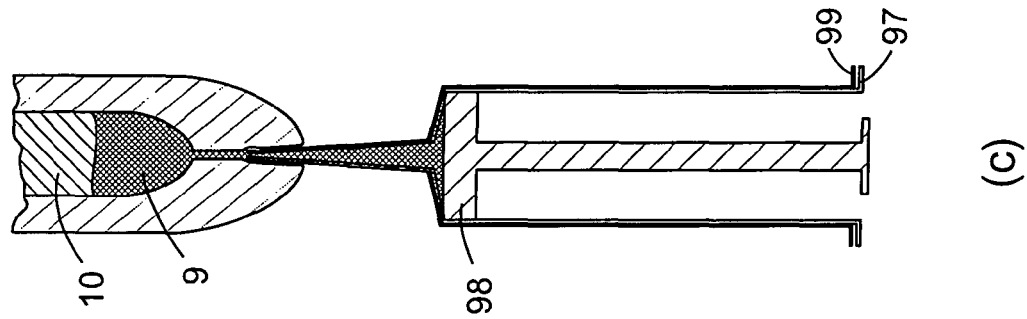
FIGS. 20(*a*) to 20(*c*) are cross sectional views of the injector device of FIG. 19, in use.
Figure 20:
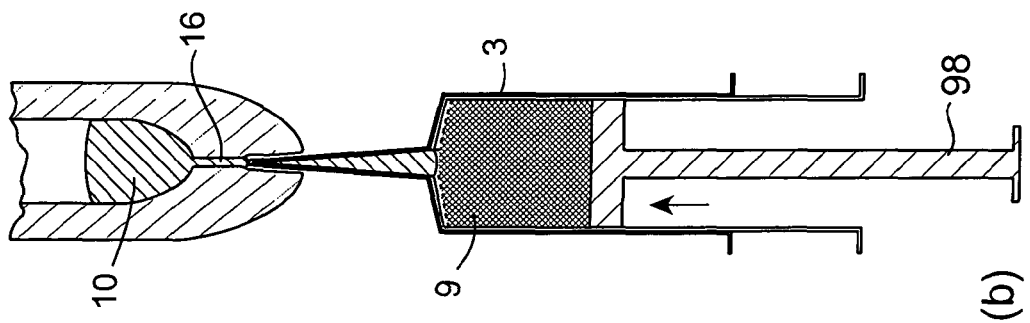
Figure 20:
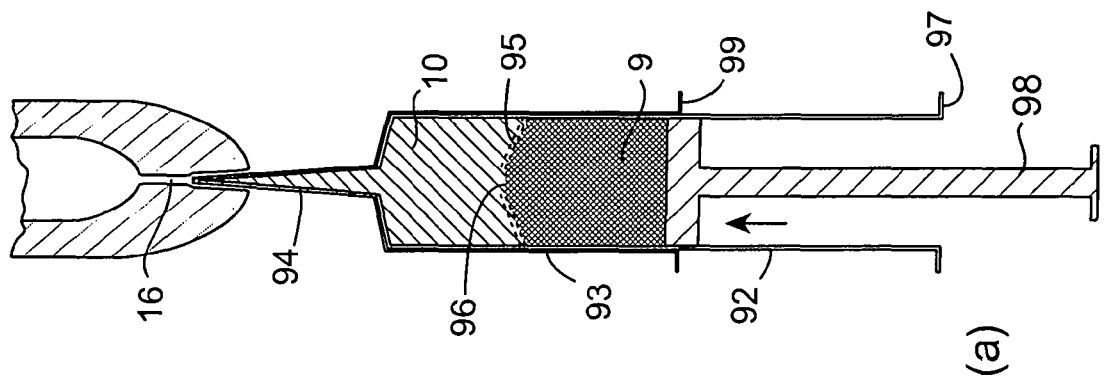

Referring to FIGS. 19 and 20 there is illustrated another injector device 90 of the invention. The injector device 90 comprises an inner barrel 92 and an outer barrel 93. The outer barrel 93 has a nozzle 94. The inner barrel 92 comprises a breakable/burstable barrier or membrane at its distal end and a plunger 98 at its proximal end. Antimicrobial 10 is contained within the outer barrel 93. In use, the nozzle 94 is inserted into a teat canal 16. The inner barrel 92 is pushed through the outer barrel 93 to expel the antimicrobial (FIG. 20(b)). This procedure may be facilitated by a flange 97 around the proximal end of the inner barrel 92 and a flange 99 around the proximal end of the outer barrel 93. When the antimicrobial 10 has been expelled (FIG. 20(c)) the plunger 98 on the inner barrel 92 is depressed to expel the seal 9 from the inner barrel 91. The pressure of the plunger 98 is sufficient to burst or rupture the barrier/membrane 96 on the inner barrel 92 allowing the seal 9 to be expelled from the injector device through the nozzle 94 and into the teat canal (FIG. 20(c)). Alternatively rupturing means such as sharp teeth situated within the outer barrel 93 at its aperture into the nozzle, ruptures the barrier/membrane 96.

A seal 96 may be provided at the front end of the inner injector barrel 92 to provide a positive seal. The inner injector may be moulded with a weak burstable barrier/membrane 95 across the outlet aperture.

It will be appreciated that the seal portion of the formulation may be manufactured in one facility and subsequently combined with the anti-bacterial portion of the formulation at a later stage, in the same or another facility.

The invention is not limited to the embodiments hereinbefore described which may be varied in detail.

The invention claimed is:

1. An injector device for delivery of components into the teat canal of a non-human animal comprising:
   a proximal end, a distal end, and a longitudinal axis defining a longitudinal direction,
   a barrel for containing a first component,
   an outlet nozzle located at a distal end of the barrel and configured for insertion into a teat canal,
   an internal receptacle within the barrel for containing a second component to be injected into the teat canal,
   a valve for separating the first component and the second component, the valve having
      a valve body having at least one passageway,
      a valve seating surface located on the internal receptacle, the valve seating surface configured to form a seal with the valve body in a valve closed position, and
   an activator including at least one projecting member coupled to the barrel at a location adjacent the outlet nozzle and extending proximally toward the delivery member, the projecting member configured to open the valve to allow the second component to be released from the internal receptacle, and
   a delivery member arranged to deliver the first component from the barrel and engage the valve body into contact with the at least one projecting member of the activator to displace the valve body proximally away from the valve seating surface in order to open the at least one passageway,
   sequential delivery of the second component from the internal receptacle through the outlet nozzle occurring upon further depression of the delivery member,
   the barrel forming an outer barrel and the internal receptacle including an inner barrel located within the outer barrel, the inner barrel including a close fit within the outer barrel so as to form a plunger to be pushed through the outer barrel by the delivery member for delivery of the first component.

2. The injector device as claimed in claim 1 wherein the activator comprises one or more passageways.

3. The injector device as claimed in claim 1 wherein the activator is configured for engagement with the internal receptacle to provide a direct passageway for delivery of the second component from the internal receptacle into the outlet nozzle.

4. The injector as claimed in claim 1 wherein the delivery member comprises a plunger for the inner barrel.

5. The injector as claimed in claim 1 wherein the inner barrel comprises an engagement member arranged to engage with the outer barrel.

6. The injector as claimed in claim 5 wherein the engagement member comprises an external seal.

7. The injector as claimed in claim 5 wherein the outer barrel comprises an engagement member arranged to engage with the inner barrel.

8. The injector as claimed in claim 7 wherein the outer barrel comprises a locking ring for engagement with the inner barrel.

9. The injector as claimed in claim 1 wherein the inner barrel comprises an engagement member arranged to engage with the delivery member.

10. The injector as claimed in claim 9 wherein the inner barrel comprises a locking ring for engagement with the delivery member.

11. The injector device as claimed in claim 1 wherein the first component comprises an antimicrobial formulation.

12. The injector device as claimed in claim 11 wherein the antimicrobial is selected from any one or more of beta-lactam antibiotics, polymyxins, glycopeptides, aminoglycosides, lincosamides, macrolides, pleuromutilins, "fenicols" including chloramphenicol and florfenicol, tetracyclines, sulphonamides and potentiated sulphonamides including mixtures of trimethoprim and one or more sulphonamide, quinolones and fluoroquinolones, ionophores, courmarins including novobiocin, natural or synthetic peptides, aminoglycosides, antimicrobial peptides or antimicrobials, lantibiotics, or other products of bacteria and other micro-organisms.

13. The injector device as claimed in claim 12 wherein the beta-lactam is selected from any one or more of penicillin, modified penicillin including cloxacillin, amoxycillin, ampicillin, cephalosporins or beta-lactam antibiotics potentiated by beta-lactamase inhibitors including clavulanic acid.

14. The injector device as claimed in claim 12 wherein the aminoglycoside is selected from any one or more of streptomycin, dihydrostreptomycin, neomycin, gentamycin, framycetin, aparamycin or kanamycin.

15. The injector device as claimed in claim 11 wherein the antimicrobial is selected from any one or more of macrolide, lincosamide or pleuromutilin, erythromycin, spiramycin, tylosin, spiramycin, tilmicosin, lincomycin, spectinomycin, pirlimycin or tiamulin.

16. The injector device as claimed in claim 11 wherein the antimicrobial is selected from any one or more of potentiated sulphonamide mixtures, trimethoprim plus sulphadiazine, sulphadimidine, sulphadoxine, sulphadimethoxine or other sulphonamide, oxytetracycline, minocycline or doxycycline, fluoroquinolones, enrofloxacin, ciprofloxacin, norfloxacin, danofloxacin, difloxacin or marbofloxacin.

17. The injector device as claimed in claim 1 wherein the second component comprises a seal formulation.

18. The injector device as claimed in claim 17 wherein the seal formulation comprises a non-toxic heavy metal salt.

19. The injector device as claimed in claim 18 wherein the seal formulation comprises greater than 40% by weight of the heavy metal salt.

20. The injector device as claimed in claim 18 wherein the seal formulation comprises between 50% and 75% by weight of the heavy metal salt.

21. The injector device as claimed in claim 18 wherein the seal formulation comprises approximately 65% by weight of the heavy metal salt.

22. The injector device as claimed in claim 18 wherein the heavy metal is bismuth.

23. The injector device as claimed in claim 18 wherein the salt is a sub-nitrate salt.

24. The injector device as claimed in claim 17 wherein the seal formulation comprises a gel base.

25. The injector device as claimed in claim 24 wherein the gel base is a gel based on aluminium stearate.

26. The injector device as claimed in claim 24 wherein the gel base includes liquid paraffin as a vehicle.

27. The injector device as claimed in claim 1 wherein the first component is delivered from the barrel and the second component is subsequently delivered from the internal receptacle without substantial mixing of the components.

28. The injector device as claimed in claim 1 wherein the first component comprises an anti-inflammatory.

29. The injector device as claimed in claim 28 wherein the anti-inflammatory is selected from any one or more of steroids including prednisolone, betamethazone, dexamethazone, phenylbutazone, or non-steroids such as flunixin, ketoprofen, carprofen, vedaprofen, meloxicam, tepoxalin, eltenac, nimesulide or tolfenamic acid.

30. An injector device for delivery of components into the teat canal of a non-human animal comprising:
a proximal end, a distal end, and a longitudinal axis defining a longitudinal direction,
a barrel for containing a first component,
an outlet nozzle located at a distal end of the barrel and configured for insertion into a teat canal,
an internal receptacle within the barrel for containing a second component to be injected into the teat canal, the internal receptacle including a distal end having an outlet,
a valve for separating the first component and the second component, the valve having
a valve body having at least one passageway, the at least one passageway extending substantially perpendicular to the longitudinal direction, and wherein a portion of the valve body is positioned within the outlet of the internal receptacle,
a valve seating surface located on an inner surface of the internal receptacle, the valve seating surface configured to form a seal with the valve body in a valve closed position, and
an activator including at least one projecting member coupled to the barrel at a location adjacent the outlet nozzle and extending proximally toward the delivery member, the projecting member configured to open the valve to allow the second component to be released from the internal receptacle, the at least one projecting member defining a substantially cylindrical form, and
a delivery member arranged to deliver the first component from the barrel and engage the valve body into contact with the at least one projecting member of the activator to displace the valve body proximally away from the valve seating surface in order to open the at least one passageway,
sequential delivery of the second component from the internal receptacle through the outlet nozzle occurring upon further depression of the delivery member,
the barrel forming an outer barrel and the internal receptacle including an inner barrel located within the outer barrel, the inner barrel including a close fit within the outer barrel so as to form a plunger to be pushed through the outer barrel by the delivery member for delivery of the first component.

31. An injector device for delivery of components into the teat canal of a non-human animal comprising:
a proximal end, a distal end, and a longitudinal axis defining a longitudinal direction,
a barrel for containing a first component,
an outlet nozzle located at a distal end of the barrel and configured for insertion into a teat canal,
an internal receptacle within the barrel for containing a second component to be injected into the teat canal,
a valve for separating the first component and the second component, the valve having
a valve body having at least one passageway,
a valve seating surface located on the internal receptacle, the valve seating surface configured to form a seal with the valve body in a valve closed position, and
an activator including at least one projecting member coupled to the barrel at a location adjacent the outlet nozzle and extending proximally toward the delivery member, the projecting member configured to open the valve to allow the second component to be released from the internal receptacle, and
a delivery member arranged to deliver the first component from the barrel and engage the valve body into contact with the at least one projecting member of the activator to displace the valve body proximally away from the valve seating surface in order to open the at least one passageway,
sequential delivery of the second component from the internal receptacle through the outlet nozzle occurring upon further depression of the delivery member, wherein the valve body achieves a fully displaced position when the internal receptacle is adjacent the distal end of the barrel,
the barrel forming an outer barrel and the internal receptacle including an inner barrel located within the outer barrel, the inner barrel including a close fit within the outer barrel so as to form a plunger to be pushed through the outer barrel by the delivery member for delivery of the first component.

* * * * *